United States Patent
Panandiker et al.

(10) Patent No.: US 8,937,142 B2
(45) Date of Patent: Jan. 20, 2015

(54) POLYSILOXANE COPOLYMERS

(71) Applicant: The Procter & Gamble Company, Cincinnati, OH (US)

(72) Inventors: Rajan Keshav Panandiker, West Chester, OH (US); Steven Daryl Smith, Fairfield, OH (US); Bernard William Kluesener, Harrison, OH (US); Carola Barrera, West Chester, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 13/951,492

(22) Filed: Jul. 26, 2013

(65) Prior Publication Data

US 2014/0030205 A1    Jan. 30, 2014

Related U.S. Application Data

(60) Provisional application No. 61/676,646, filed on Jul. 27, 2012.

(51) Int. Cl.
| | | |
|---|---|---|
| *C08G 77/26* | (2006.01) | |
| *C08G 77/452* | (2006.01) | |
| *C08G 77/54* | (2006.01) | |
| *D06M 15/647* | (2006.01) | |
| *D06M 15/643* | (2006.01) | |
| *A61Q 5/02* | (2006.01) | |
| *A61Q 5/12* | (2006.01) | |
| *A61K 8/898* | (2006.01) | |

(52) U.S. Cl.
CPC .............. *C08G 77/26* (2013.01); *C08G 77/54* (2013.01); *D06M 15/647* (2013.01); *D06M 15/6436* (2013.01); *A61Q 5/02* (2013.01); *A61Q 5/12* (2013.01); *A61K 8/898* (2013.01)

USPC ............. 528/27; 528/28; 528/38; 510/466; 510/475; 424/70.122

(58) Field of Classification Search
USPC .............. 528/28, 27, 38; 510/466, 475; 424/70.122
See application file for complete search history.

(56) References Cited

U.S. PATENT DOCUMENTS

| | | | |
|---|---|---|---|
| 5,879,584 A | | 3/1999 | Bianchetti et al. |
| 6,608,126 B2 * | | 8/2003 | Ferritto et al. ............... 524/266 |
| 6,855,680 B2 | | 2/2005 | Smerznak et al. |
| 7,294,611 B2 | | 11/2007 | Metrot et al. |
| 8,158,572 B2 * | | 4/2012 | Schubert et al. ............. 510/466 |
| 2008/0194785 A1 * | | 8/2008 | Wagner et al. ................. 528/27 |
| 2012/0308494 A1 * | | 12/2012 | Schubert et al. ............... 424/59 |

FOREIGN PATENT DOCUMENTS

WO   WO 01/05874 A1   1/2001

OTHER PUBLICATIONS

International Search Report; International Application No. PCT/US2013/052156; Date of mailing Jan. 7, 2014; 10 pages.

* cited by examiner

*Primary Examiner* — Margaret Moore
(74) *Attorney, Agent, or Firm* — James F. McBride; Steven W. Miller

(57) ABSTRACT

The present application relates to polysiloxane copolymers and compositions such as consumer products comprising such polysiloxane copolymers, as well as processes for making and using such polysiloxane copolymers and such compositions. When employed as taught, such polysiloxane copolymers and compositions comprising same provide enhanced softness, wrinkle reduction, color benefits, smoothness, static control, and shine.

9 Claims, No Drawings

POLYSILOXANE COPOLYMERS

FIELD OF INVENTION

The present application relates to polysiloxane copolymers and compositions such as consumer products comprising such polysiloxane copolymers, as well as processes for making and using such polysiloxane copolymers and such compositions.

BACKGROUND OF THE INVENTION

Silicones are used in premium consumer products to deliver benefits such as softness, hand, anti-wrinkle, hair conditioning/frizz control, color protection etc. Unfortunately, silicones, including current organosilicones, are expensive, difficult to process, and may lack the required chemical and/or physical stability. Typically, such physical and/or chemical stability problems manifest themselves as creaming and/or discoloration of a consumer product that comprises silicone. In addition, such discoloration may not only occur in product but also on surfaces that are treated with the consumer product that comprises the silicone. Current silicone technologies are expensive due to the cost of silicone raw materials and the silicone emulsification step that is required to make such silicones useful in products. Thus, what is needed is an economical silicone technology that has the required chemical and physical stability when used in a consumer product.

Fortunately, Applicants recognized that contrary to current wisdom that terminal primary aminosilicone polymers can be used to produce polysiloxane copolymers. In short, Applicants discovered that by judiciously selecting the appropriate processing conditions and reactants—including terminal primary aminosiloxane polymers, highly effective, economical polysiloxane copolymers can be obtained.

SUMMARY OF THE INVENTION

The present application relates to polysiloxane copolymers and compositions such as consumer products comprising such polysiloxane copolymers, as well as processes for making and using such polysiloxane copolymers and such compositions.

DETAILED DESCRIPTION OF THE INVENTION

Definitions

As used herein "consumer product" means baby care, beauty care, fabric & home care, family care, feminine care, health care, personal care products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "situs" includes paper products, fabrics, garments, hard surfaces, hair and skin.

As used herein random means that the units of the polymer are randomly distributed throughout the polymer chain.

As used herein blocky means that multiple units the polymer are placed end to end throughout the polymer chain.

When a moiety or an indice of a preferred embodiment is not specifically defined, such moeity or indice is as previously defined.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

In one aspect, a polysiloxane copolymer having the following structure:

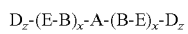

wherein:
each index x is independently an integer from 1 to 20, from 1 to 12, from 1 to 8, or from 2 to 6, and
each z is independently 0 or 1;
A has the following structure:

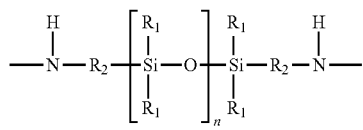

wherein:
each $R_1$ is independently a H, —OH, or $C_1$-$C_{22}$ alkyl group, in one aspect H, —OH, or $C_1$-$C_{12}$ alkyl group, H, —OH, or $C_1$-$C_2$ alkyl group, or —$CH_3$;
each $R_2$ is independently selected from a divalent $C_1$-$C_{22}$ alkylene radical, a divalent $C_2$-$C_{12}$ alkylene radical, a divalent linear $C_2$-$C_8$ alkylene radical, or a divalent linear $C_3$-$C_4$ alkylene radical;
the index n is an integer from 1 to about 5,000, from about 10 to about 1,000, from about 25 to about 700, from about 100 to about 500, or from about 450 to about 500;

each B is independently selected from the following moieties:

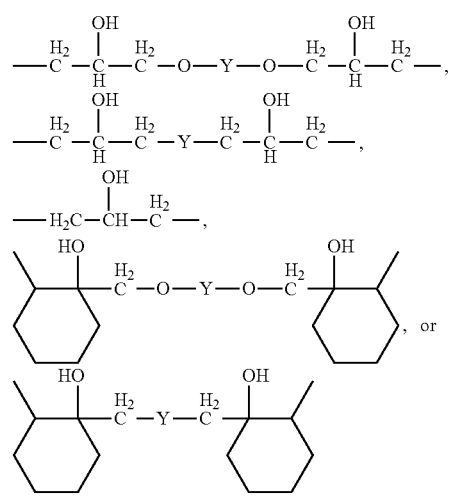

wherein for each structure, Y is a divalent $C_2$-$C_{22}$ alkylene radical that is optionally interrupted by one or more heteroatoms selected from the group consisting of O, P, S, N and combinations thereof or a divalent $C_8$-$C_{22}$ aryl alkylene radical, in one aspect a divalent $C_2$-$C_8$ alkylene radical that is optionally interrupted by one or more heteroatoms selected from the group consisting of O, P, S, N and combinations thereof or a divalent $C_8$-$C_{16}$ aryl alkylene radical, in one aspect a divalent $C_2$-$C_6$ alkylene radical that is optionally interrupted by one or more heteroatoms selected from the group consisting of O, N and combinations thereof or a divalent $C_8$-$C_{12}$ aryl alkylene radical;

each E is independently selected from the following moieties:

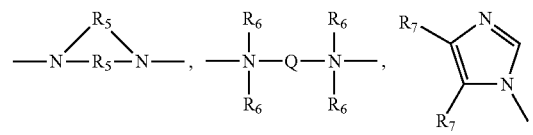

wherein:
each $R_5$ and each Q is independently selected from a divalent $C_1$-$C_{12}$ linear or branched aliphatic hydrocarbon radical that is optionally interrupted by one or more heteroatoms selected from the group consisting of O, P, S, N and combinations thereof, in one aspect a divalent $C_1$-$C_8$ linear or branched aliphatic hydrocarbon radical that is optionally interrupted by one or more heteroatoms selected from the group consisting of O, P, S, N and combinations thereof, in one aspect a divalent $C_1$-$C_3$ linear or branched aliphatic hydrocarbon radical that is optionally interrupted by one or more heteroatoms selected from the group consisting of O, N and combinations thereof;
each $R_6$ and $R_7$ is independently selected from H, $C_1$-$C_{20}$ alkyl, $C_1$-$C_{20}$ substituted alkyl, $C_6$-$C_{20}$ aryl, and $C_6$-$C_{20}$ substituted aryl, in one aspect H, $C_1$-$C_{12}$ alkyl, $C_1$-$C_{12}$ substituted alkyl, $C_6$-$C_{12}$ aryl, and $C_6$-$C_{12}$ substituted aryl, H, in one aspect $C_1$-$C_3$ alkyl, $C_1$-$C_3$ substituted alkyl, $C_6$ aryl, and $C_6$ substituted aryl, or H, with the proviso that at least one $R_6$ on each of the nitrogen atoms is H; and when E is selected from

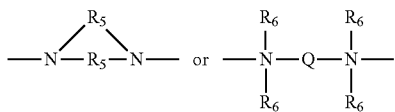

and when z is 1, the respective D is selected from H, —CH$_3$, or $R_6$; when E is

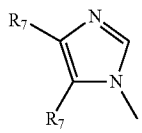

z is 0 and B is

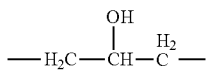

is disclosed.

Compositions Comprising Polysiloxane Copolymer

In one aspect, a composition that comprises the aforementioned polysiloxane copolymer and comprising at least one additional component selected from the group consisting of emollients, emulsifiers and surfactants, thickeners/viscosity regulators/stabilizers, UV light protection filters, antioxidants, hydrotropes or polyols, solids and fillers, film formers, pearlescent additives, insect repellents, preservatives, conditioners, perfumes, dyes, care additives, solvents, perfume delivery systems, fluorescent whitening agents, enzymes, rheology modifiers, builders, bleaching agents, bleach activators, bleach boosters, chelants, stabilizers, softening actives, high melting point fatty compounds, polymers, anti-dandruff actives, humectants, suspending agents, skin care actives, color cosmetics, and mixtures thereof is disclosed.

In one aspect, said composition comprises, based on total composition weight, from about 0.01% to about 70%, from about 0.1% to about 50%, from about 0.5% to about 10%, from about 0.7% to about 7%, or from about 1% to about 5% of said polysiloxane copolymer.

In one aspect, said composition comprises a polysiloxane copolymer having the following structure:

D-(E-B)$_x$-A-(B-E)$_x$-D wherein:
each index x is independently an integer from 1 to 20, from 1 to 12, from 1 to 8, or from 2 to 6;
A has the following structure:

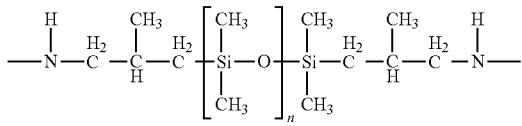

wherein:
the index n is from about 250 to about 700;

each B is independently selected from a moiety having the following structure:

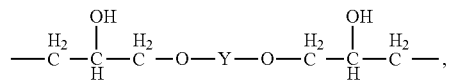

wherein Y is a divalent $C_2$-$C_6$ alkylene radical;
each E is

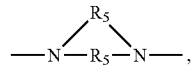

wherein each $R_5$ is —CH$_2$CH$_2$—:
each D is H.

In one aspect, said composition comprises a polysiloxane copolymer that comprises a quaternizing moiety selected from the group consisting of $C_1$-$C_{30}$ alkyl halide, $C_1$-$C_{30}$ aryl halide, $C_1$-$C_{30}$ alkyl sulfate, and/or $C_1$-$C_{30}$ aryl sulfates.

In one aspect, said composition comprises from about 0.1% to about 50% by weight of a surfactant selected from the group consisting of anionic, cationic, amphoteric, nonionic surfactants, and combinations thereof.

In one aspect, said composition comprises a material selected from the group consisting of fluorescent whitening agents, enzymes, rheology modifiers, builders, bleaching agents, bleach activators, bleach boosters, chelants, and mixtures thereof, wherein the weight ratio of anionic surfactant to the sum of cationic, amphoteric, and nonionic surfactants is from about 10:1 to about 1:10, from about 6:1 to about 1:9 or from about 5:1 to 1:2 and the total weight percent of surfactant is said composition is from about 5% to about 50%, or from about 7% to about 30%.

In one aspect, said composition comprises one or more adjuncts selected from the group consisting of:
a) an anionic surfactant selected from the group consisting of a $C_{11}$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, alkyls, alkyl ether sulfates, succinnates, olefin sulfonates, beta-alkyloxy alkane sulfonates and mixtures thereof,
b) a cationic surfactant selected from the group consisting of mono-long alkyl quaternized ammonium salt cationic surfactants, mono-alkyl amines, di-alkyl chain cationic surfactants, and mixtures thereof,
c) a conditioning active selected from the group consisting of silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein,
d) a perfume delivery system selected from a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, a pro-perfume, low odor detection threshold perfume ingredients, wherein said low odor detection threshold perfume ingredients may comprise less than about 25%, by weight of the total neat perfume composition, and mixtures thereof, e) a perfume comprising a perfume raw material selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, α-damascone, β-damascone, δ-damascone, β-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol, f) a softening active selected from the group consisting of from the group consisting of polyglycerol esters, oily sugar derivatives, wax emulsions, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate and mixtures thereof, g) a deposition aid polymer selected from the group consisting of starch, guar, cellulose, cassia, locust bean, Konjac, Tara, galactomannan, polyDADMAC, Tapioca starch, polyTriquat, and mixtures thereof, h) a deposition aid polymer selected from the group consisting of a cationic polymer having a cationic charge from about 0.005 meq/g to about 23 meq/g, from about 0.01 meq/g to about 12 meq/g, from about 0.1 meq/g to about 7 meq/g at the pH of said composition, i) a high melting point fatty compound selected from the group consisting of fatty alcohols, fatty acids, fatty alcohol derivatives, fatty acid derivatives, and mixtures thereof.

said materials from a) above are useful in Hair Care and Laundry products, said materials from b) above are useful in Hair Care including Shampoo and Conditioner products, said materials from c) above are useful in Hair Conditioning products, said materials from d) and e) above are useful in consumer products including Hair Care and Laundry products, materials from f) above are useful in fabric treatment products, including fabric enhancers, said materials from g) above are useful in Hair Care products, said materials from h) above are useful in Fabric Care products, and said materials from i) above are useful in Hair Care products.

In one aspect two or more of the previous aspects of said composition may be combined to form a separate aspect of said composition.

Process of Making Polysiloxane Copolymers

In one aspect, a process of making polysiloxane copolymers comprises reacting a diepoxide and/or epichlorohydrin; a diamine said diamine's amines comprising secondary amines; a primary terminal aminosilicone; and optionally a capping reactant comprising an amino group is disclosed.

In one aspect, said diamine's amines are secondary amines.

In one aspect of said process said diepoxide-diamine oligomer and/or epichlorohydrin-diamine oligomer is reacted with said primary terminal amino silicone.

In one aspect of said process said diepoxide-diamine oligomer and/or epichlorohydrin-diamine oligomer is formed by first reacting said diepoxide and/or epichlorohydrin with said diamine.

In one aspect of said process said reaction is carried out at a temperature from about 0° C. to about 200° C., from about 25° C. to about 160° C., from about 35° C. to about 140° C., or from about 40° C. to about 120° C.

In one aspect of said process the ratio of diepoxide and/or epichlorohydrin to diamine to primary terminal aminosilicone is from about 1:1:1 to about 102:100:1, from about 2:2:1 to about 42:40:1, from about 4:4:1 to about 22:20:1, or from about 6:6:1 to about 12:10:1.

In one aspect of said process the primary aminosilicone has the following structure:

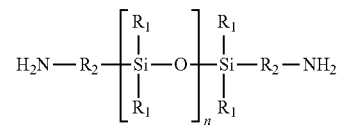

wherein:
each $R_1$ is independently a H, —OH, or $C_1$-$C_{22}$ alkyl group, in one aspect H, —OH, or $C_1$-$C_{12}$ alkyl group, H, —OH, or $C_1$-$C_2$ alkyl group, or —$CH_3$;
each $R_2$ is independently selected from a divalent $C_1$-$C_{22}$ alkylene radical, a divalent $C_2$-$C_{12}$ alkylene radical, a divalent linear $C_2$-$C_8$ alkylene radical, or a divalent linear $C_3$-$C_4$ alkylene radical;
the index n is an integer from 1 to about 5,000, from about 10 to about 1,000, from about 25 to about 700, from about 100 to about 500, or from about 450 to about 500;
the diepoxide or epichlorohydrin is selected from one or more of the following materials:

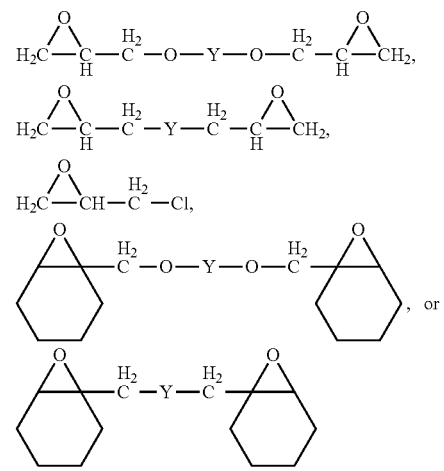

wherein for each structure, Y is a divalent $C_2$-$C_{22}$ alkylene radical that is optionally interrupted by one or more heteroatoms selected from the group consisting of O, P, S, N and combinations thereof or a divalent $C_8$-$C_{22}$ aryl alkylene radical, in one aspect a divalent $C_2$-$C_8$ alkylene radical that is optionally interrupted by one or more heteroatoms selected from the group consisting of O, P, S, N and combinations thereof or a divalent $C_8$-$C_{16}$ aryl alkylene radical, in one aspect a divalent $C_2$-$C_6$ alkylene radical that is optionally interrupted by one or more heteroatoms selected from the group consisting of O, N and combinations thereof or a divalent $C_8$-$C_{12}$ aryl alkylene radical;

the diamine is independently selected from the following materials:

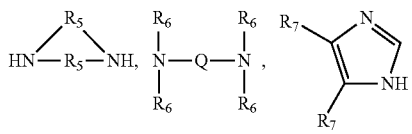

wherein:
each $R_5$ and each Q is independently selected from a divalent $C_1$-$C_{12}$ linear or branched aliphatic hydrocarbon radical that is optionally interrupted by one or more heteroatoms selected from the group consisting of O, P, S, N and combinations thereof, in one aspect a divalent $C_1$-$C_8$ linear or branched aliphatic hydrocarbon radical that is optionally interrupted by one or more heteroatoms selected from the group consisting of O, P, S, N and combinations thereof, in one aspect a divalent $C_1$-$C_3$ linear or branched aliphatic hydrocarbon radical that is optionally interrupted by one or more heteroatoms selected from the group consisting of O, N and combinations thereof;
each $R_6$ and $R_7$ is independently selected from H, $C_1$-$C_{20}$ alkyl, $C_1$-$C_{20}$ substituted alkyl, $C_6$-$C_{20}$ aryl, and $C_6$-$C_{20}$ substituted aryl, in one aspect H, $C_1$-$C_{12}$ alkyl, $C_1$-$C_{12}$ substituted alkyl, $C_6$-$C_{12}$ aryl, and $C_6$-$C_{12}$ substituted aryl, H, in one aspect $C_1$-$C_3$ alkyl, $C_1$-$C_3$ substituted alkyl, $C_6$ aryl, and $C_6$ substituted aryl, or H, with the proviso that at least one $R_6$ on each of the nitrogen atoms is H.

In one aspect of said process the primary aminosilicone has the following structure:

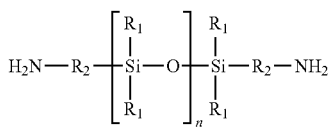

wherein:
each $R_1$ is —$CH_3$,
each $R_2$ is a divalent linear $C_3$-$C_4$ alkylene radical;
the index n is an integer from about 450 to about 500;
the diepoxide or epichlorohydrin is:

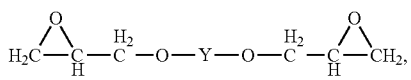

wherein for each structure, Y is a divalent $C_2$-$C_6$ alkylene radical;
the diamine is:

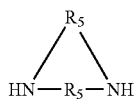

wherein:
each $R_5$ is a divalent $C_1$-$C_3$ linear or branched aliphatic hydrocarbon radical.

In one aspect of said process using a catalyst to catalyze said reaction, said catalyst being selected from the group consisting of a protic solvent, a metallic catalyst, and mixtures thereof is disclosed.

In one aspect of said process comprises quaternizing said polysiloxane copolymer.

Catalysts—Suitable catalysts for making the polysiloxane copolymers of the present invention include, but are not limited to, metallic catalysts, and protic solvents. The term "metallic catalyst" includes within its definition catalysts which include a metallic component. This definition includes metallic salts and materials such as $AlCl_3$, covalent compounds, and materials such as $BF_3$ and $SnCl_4$, all of which include a metallic component. The metallic component includes all elements commonly known as metals, such as alkali metals, alkaline earth metals, transition metals, and boron.

Suitable catalysts include, but are not limited to, $TiCl_4$, $Ti(OiPr)_4$, $ZnCl_2$, $SnCl_4$, $SnCl_2$, $FeCl_3$, $AlCl_3$, $BF_3$, platinum dichloride, copper(II) chloride, phosphorous pentachloride, phosphorous trichloride, cobalt(II) chloride, zinc oxide, iron (II) chloride and $BF_3$—$OEt_2$ and mixtures thereof. In some aspects, the metallic catalysts are Lewis acids. The metallic components of these Lewis acid catalysts include Ti, Zn, Fe, Sn, B, and Al. Suitable Lewis acid catalysts include $TiCl_4$, $SnCl_4$, $BF_3$, $AlCl_3$, and mixtures thereof. In some aspects, the catalyst is $SnCl_4$ or $TiCl_4$. The metallic Lewis acid catalysts may be employed at concentrations of about 0.1 mol % to about 5.0 mol %, in some aspects, about 0.2 mol % to about 1.0 mol %, in some aspects about 0.25 mol %.

Other suitable catalysts for making the organosilicones include basic or alkaline catalysts. The term "basic catalyst" includes within its definition catalysts which are basic or alkaline. This definition includes alkaline salts and materials such as KH, KOH, KOtBu, NaOEt, covalent compounds, and elements, such as metallic sodium.

Suitable catalysts include alkali metal alkoxylates, such as KOtBu, NaOEt, KOEt, NaOMe and mixtures thereof, NaH, NaOH, KOH, CaO, CaH, $Ca(OH)_2$, $Ca(OCH(CH_3)_2)_2$, Na and mixtures thereof. In some aspects, the catalyst is selected from alkali metal alkoxylates. In some aspects, the basic catalyst is a Lewis base. Suitable Lewis base catalysts include KOH, $NaOCH_3$, $NaOC_2H_5$, KOtBu, NaOH, and mixtures thereof. The Lewis base catalysts may be employed at concentrations of about 0.1 mol % to about 5.0 mol %, in some aspects, about 0.2 mol % to about 1.0 mol %. The alkali metal alkoxylate catalysts may be employed at concentrations of about 2.0 mol % to about 20.0 mol %, in some aspects, about 5.0 mol % to about 15.0 mol %.

Protic solvents are solvents that have a hydrogen atom bonded to an electronegative atom, yielding highly polarized bonds in which the hydrogen has proton-like character and can have hydrogen bonding characteristics. In one aspect said protic solvent is selected from the group consisting of diols, triols, polyols, water, a water/surfactant mixture and mixtures thereof. In one aspect said diol is selected from the group consisting of ethylene glycol, 1,2-propanediol, 1,3-propanediol, 2-methyl-1,3-propanediol, 2,2-dibutyl-1,3-propanediol, 2,2-diethyl-1,3-propanediol, 2-methylene-1,3-propanediol, 3-ethoxy-1,2-propanediol, 2-methyl-2-propyl-1,3-propanediol, 3-methoxy-1,2-propanediol, 1,2-butanediol, 1,3-butanediol, 1,4-butanediol, 2,3-butanediol, 1,2-pentanediol, 1,4-pentanediol, 1,5-pentanediol, 2,4-pentanediol, 1,2-hexanediol, neopentyl glycol, 1,5-hexanediol, 1,6-hexanediol, 2,5-hexanediol, 1,7-heptanediol, 1,4-heptanediol, 2-hydroxymethyl-1,3-propanediol 1,2-octanediol, 1,8-octanediol, 4,5-octanediol, 1,9-nonanediol, 1,10-decanediol, 1,2-decanediol, 1,2-dodecanediol, 1,12-dodecanediol, 1,14-tetradecanediol, 1,2-tetradecanediol, 1,16-hexadecanediol, 1,2-hexadecanediol, 1,2-octadecanediol, 1,18-octadecanediol, and glycerol monoethers and mixtures thereof. In one aspect said glycerol monoethers are selected from the group consisting of 3-propoxypropane-1,2-diol, batyl alcohol and mixtures thereof. In one aspect said triol is selected from the group consisting of glycerol, ethoxylated glycerol, propoxylated glycerol, alkoxyated glycerol, 1,1,1-tris(hydroxymethyl)ethane, 1,1,1-tris(hydroxymethyl)propane, 2-hydroxymethyl-1,3-propanediol, 1,2,4-butanetriol, 1,2,4-butanetriol, 3-methyl-1,3,5-pentanetriol, 1,2,3-hexanetriol, 1,2,6-hexanetriol, 1,2,3-heptanetriol, 1,2,3-octanetriol and mixtures thereof. In one aspect said polyol is selected from the group consisting of pentaerythritol, alkoxylated pentaerythritol, sorbitol, alkoxylated sorbitol, glucose, alkoxylated glucose, fructose, alkoxylated fructoses, and mixtures thereof. In one aspect said catalyst is selected from:
 a) alkoxylated pentaerythritol is selected from the group consisting of ethoxylated pentaerythritol, proxylated pentaerythritol, and mixtures thereof;
 b) alkoxylated sorbitol is selected from the group consisting of ethoxylated sorbitol, proxylated sorbitol and mixtures thereof;
 c) alkoxylated glucose is selected from the group consisting of ethoxylated glucose, proxylated glucose, and mixtures thereof;
 d) alkoxylated fructose is selected from the group consisting of ethoxylated fructose, proxylated fructose and mixtures thereof;
 e) and mixtures thereof.

In one aspect said polyol is selected from the group consisting of a sugar, a carbohydrate, an alkoxylated sugar, an alkoxylated carbohydrate and mixtures thereof.

Method of Use

In one aspect a method of treating and/or cleaning a situs, said method comprising
 a.) optionally washing, rinsing and/or drying said situs;
 b.) contacting said situs with any of the polysiloxane copolymer containing compositions disclosed herein; and
 c.) optionally washing, rinsing and/or drying said situs.
Said drying may be passive drying and/or active drying. For example, active drying via a laundry dryer.

Consumer Product Adjunct Materials

The disclosed compositions may include additional adjunct ingredients that include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. Other embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

Deposition Aid—In one aspect, the fabric treatment composition may comprise from about 0.01% to about 10%, from about 0.05 to about 5%, or from about 0.15 to about 3% of a deposition aid. In one aspect, the deposition aid may be a cationic or amphoteric polymer. In another aspect, the deposition aid may be a cationic polymer. Cationic polymers in general and their method of manufacture are known in the literature. In one aspect, the cationic polymer may have a cationic charge density of from about 0.005 to about 23 meq/g, from about 0.01 to about 12 meq/g, or from about 0.1 to about 7 meq/g, at the pH of the composition. For amine-containing polymers, wherein the charge density depends on the pH of the composition, charge density is measured at the intended use pH of the product. Such pH will generally range from about 2 to about 11, more generally from about 2.5 to about 9.5. Charge density is calculated by dividing the number of net charges per repeating unit by the molecular weight of the repeating unit. The positive charges may be located on the backbone of the polymers and/or the side chains of polymers.

In another aspect, the deposition aid may comprise a cationic acrylic based polymer. In a further aspect, the deposition aid may comprise a cationic polyacrylamide. In another aspect, the deposition aid may comprise a polymer comprising polyacrylamide and polymethacrylamidopropyl trimethylammonium cation. In another aspect, the deposition aid may comprise poly(acrylamide-N-dimethyl aminoethyl acrylate) and its quaternary derivatives.

In another aspect, the deposition aid may be selected from the group consisting of cationic or amphoteric polysaccharides. In one aspect, the deposition aid may be selected from the group consisting of cationic and amphoteric cellulose ethers, cationic or amphoteric galactomannan, cationic guar gum, cationic or amphoteric starch, and combinations thereof.

Another group of suitable cationic polymers may include alkylamine-epichlorohydrin polymers which are reaction products of amines and oligoamines with epichlorohydrin. Another group of suitable synthetic cationic polymers may include polyamidoamine-epichlorohydrin (PAE) resins of polyalkylenepolyamine with polycarboxylic acid. The most common PAE resins are the condensation products of diethylenetriamine with adipic acid followed by a subsequent reaction with epichlorohydrin.

The weight-average molecular weight of the polymer may be from about 500 Daltons to about 5,000,000 Daltons, or from about 1,000 Daltons to about 2,000,000 Daltons, or from about 2,500 Daltons to about 1,500,000 Daltons, as determined by size exclusion chromatography relative to polyethylene oxide standards with RI detection. In one aspect, the MW of the cationic polymer may be from about 500 Daltons to about 37,500 Daltons.

Surfactants: Surfactants utilized can be of the anionic, nonionic, zwitterionic, ampholytic or cationic type or can comprise compatible mixtures of these types. Anionic and nonionic surfactants are typically employed if the fabric care product is a laundry detergent. On the other hand, cationic surfactants are typically employed if the fabric care product is a fabric softener.

In addition to the anionic surfactant, the fabric care compositions of the present invention may further contain a nonionic surfactant. The compositions of the present invention can contain up to about 30%, alternatively from about 0.01% to about 20%, more alternatively from about 0.1% to about 10%, by weight of the composition, of a nonionic surfactant. In one embodiment, the nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

The fabric care compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric care benefits. Non-limiting examples of useful cationic surfactants include: fatty amines; quaternary ammonium surfactants; and imidazoline quat materials.

Non-limiting examples of fabric softening actives are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate; 1, 2 di (stearoyl-oxy) 3 trimethyl ammoniumpropane chloride; dialkylenedimethylammonium salts such as dicanoladimethylammonium chloride, di(hard)tallowedimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of softener actives disclosed above are suitable for use herein.

Builders—The compositions may also contain from about 0.1% to 80% by weight of a builder. Compositions in liquid form generally contain from about 1% to 10% by weight of the builder component. Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of $SiO2$ to alkali metal oxide of from about 0.5 to about 4.0, or from about 1.0 to about 2.4. Also useful are aluminosilicates including zeolites.

Dispersants—The compositions may contain from about 0.1%, to about 10%, by weight of dispersants Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners—The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Other bleaching agents include metal complexes of transitional metals with ligands of defined stability constants.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or crosslinked.

In one aspect, the organo silicone may comprise a cyclic silicone. The cyclic silicone may comprise a cyclomethicone of the formula $[(CH_3)_2SiO]_n$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In one aspect, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In another aspect, the functionalized siloxane polymer may comprise an aminosilicone.

In one aspect, the organosilicone may comprise amine ABn silicones and quat ABn silicones. Such organosilicones are generally produced by reacting a diamine with an epoxide.

In another aspect, the functionalized siloxane polymer may comprise silicone-urethanes. These are commercially available from Wacker Silicones under the trade name SLM-21200®.

Perfume: The optional perfume component may comprise a component selected from the group consisting of
  (1) a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;
  (2) a pro-perfume;
  (3) a low odor detection threshold perfume ingredients, wherein said low odor detection threshold perfume ingredients may comprise less than about 25%, by weight of the total neat perfume composition; and
  (4) mixtures thereof; and Microcapsule—The compositions may comprise from about 0.05% to about 5%; or from about 0.1% to about 1% of a microcapsule. In one aspect, the microcapsule may comprise a shell comprising a polymer crosslinked with an aldehyde. In one aspect, the microcapsule may comprise a shell comprising a polymer selected from the group consisting of polyurea, polyurethane, polyamine, urea crosslinked with an aldehyde or melamine crosslinked with an aldehyde. Examples of materials suitable for making the shell of the microcapsule include melamine-formaldehyde, urea-formaldehyde, phenol-formaldehyde, or other condensation polymers with formaldehyde.

In one aspect, the microcapsules may vary in size (i.e., the maximum diameter is from about 1 to about 75 microns, or from about 5 to about 30 microns). The capsules may have an average shell thickness ranging from about 0.05 to about 10 microns, alternatively from about 0.05 to about 1 micron.

In one aspect, the microcapsule may comprise a perfume microcapsule. In turn, the perfume core may comprise a perfume and optionally a diluent. Capsules having a perfume loading of from about 50% to about 95% by weight of the capsule may be employed.

The shell material surrounding the core to form the microcapsule can be any suitable polymeric material which is impervious or substantially impervious to the materials in the core (generally a liquid core) and the materials which may come in contact with the outer surface of the shell. In one aspect, the material making the shell of the microcapsule may comprise formaldehyde. Formaldehyde based resins such as melamine-formaldehyde or urea-formaldehyde resins are especially attractive for perfume encapsulation due to their wide availability and reasonable cost.

One method for forming shell capsules useful herein is polycondensation, which may be used to produce aminoplast encapsulates. Aminoplast resins are the reaction products of one or more amines with one or more aldehydes, typically formaldehyde. Non-limiting examples of amines are melamine and its derivatives, urea, thiourea, benzoguanamine, and acetoguanamine and combinations of amines. Suitable cross-linking agents (e.g. toluene diisocyanate, divinyl benzene, butane diol diacrylate, etc) may also be used and secondary wall polymers may also be used as appropriate, as described in the art, e.g., anhydrides and their derivatives, particularly polymers and copolymers of maleic anhydride.

Microcapsules having the liquid cores and polymer shell walls as described above can be prepared by any conventional process which produces capsules of the requisite size, friability and water-insolubility. Generally, such methods as coacervation and interfacial polymerization can be employed in known manner to produce microcapsules of the desired characteristics Porous Carrier Microcapsule—A portion of the perfume composition can also be absorbed onto and/or into a porous carrier, such as zeolites or clays, to form perfume porous carrier microcapsules in order to reduce the amount of free perfume in the multiple use fabric conditioning composition.

Pro-perfume—The perfume composition may additionally include a pro-perfume. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen.

Processes of Making Fabric and/or Hard Surface Cleaning and/or Treatment Compositions The cleaning and/or treatment compositions of the present invention can be formulated into any suitable form and prepared by any process chosen by the formulator, non-limiting examples of which are described in U.S. Pat. No. 5,879,584 which is incorporated herein by reference.

Polymer Examples and Synthesis

To a clean vessel under inert atmosphere is added an amount of amino silicone. Optionally, a solvent such as isopropanol or tetrahydrofuran is added. The reaction is optionally mixed and quantities of dyglicidyl ether or epichlorohydrin or bis(cyclohexyl epoxide) ether are added along with the diamine. The selected diamine is added second to obtain the target composition. Optionally, the dyglicidyl ether or epichlorohydrin or bis(cyclohexyl epoxide) ether is reacted first with the selected diamine to obtain the target composition and the amino silicone is added second. The reaction is run at a temperature appropriate for the reagents. Chlorides are run at temperatures typically above 60° C. and often above 80° C.

Example Polymer 1

100 grams of terminal amine functional silicone (30,000 MW; DMS-A32 available from Gelest Co., Morrisville, Pa.) is reacted with 13.48 grams of butanediol-diglycidyl ether and 5.73 grams of piperazine and 250 ml of tetrahydrofuram (available from Aldrich Chemical, Milwaukee, Wis.). The reaction is stirred at room temperature for 24 hours and then isolated by vacuum stripping.

Example Polymer 2

100 grams of terminal amine functional silicone (30,000 MW; DMS-A32 available from Gelest Co., Morrisville, Pa.) is reacted with 6.17 grams of epichlorohydrin and 5.73 grams of piperazine. and 250 ml of tetrahydrofuram (available from Aldrich Chemical, Milwaukee, Wis.). The reaction is stirred at room temperature for 24 hours and then isolated by vacuum stripping Example Polymer 3

100 grams of terminal amine functional silicone (30,000 MW; DMS-A32 available from Gelest Co., Morrisville, Pa.) is reacted with 1.35 grams of butanediol-diglycidyl ether and 0.57 grams of piperazine and 250 ml of tetrahydrofuram (available from Aldrich Chemical, Milwaukee, Wis.). The reaction is stirred at room temperature for 24 hours and then isolated by vacuum stripping Example Polymer 4

25 grams of terminal amine functional silicone (3,000 MW; DMS-A15 available from Gelest Co., Morrisville, Pa.) is reacted with 3.37 grams of butanediol-diglycidyl ether and 1.43 grams of piperazine and 250 ml of tetrahydrofuram (available from Aldrich Chemical, Milwaukee, Wis.). The reaction is stirred at room temperature for 24 hours and then isolated by vacuum stripping Example Polymer 5

25 grams of terminal amine functional silicone (3,000 MW; DMS-A15 available from Gelest Co., Morrisville, Pa.) is reacted with 16.83 grams of butanediol-diglycidyl ether and 7.17 grams of piperazine and 250 ml of tetrahydrofuram (available from Aldrich Chemical, Milwaukee, Wis.). The reaction is stirred at room temperature for 24 hours and then isolated by vacuum stripping Example Polymer 6

20.20 grams of butanediol-diglycidyl ether and 7.17 grams of piperazine are charged to a reactor with 250 grams of tetrahydrofuran (available from Aldrich Chemical, Milwaukee, Wis.). The reaction is stirred at 40° C. for 24 hours and then 25 grams of terminal amine functional silicone (3,000 MW; DMS-A15 available from Gelest Co., Morrisville, Pa.) is added to the reaction. After 24 hours at 40 C, 1 gram of piperazine is added to the reactor and the reaction is continued for another 4 hours.

Example Polymer 7

6.73 grams of butanediol-diglycidyl ether and 1.43 grams of piperazine are charged to a reactor with 250 grams of tetrahydrofuran (available from Aldrich Chemical, Milwaukee, Wis.). The reaction is stirred at room temperature for 24 hours and then 25 grams of terminal amine functional silicone (3,000 MW; DMS-A15 available from Gelest Co., Morrisville, Pa.) is added to the reaction. After 24 hours at 40° C., 1 gram of piperazine is added to the reactor and the reaction is continued for another 4 hours.

Example Polymer 8

8.08 grams of butanediol-diglycidyl ether and 2.87 grams of piperazine are charged to a reactor with 250 grams of tetrahydrofuran (available from Aldrich Chemical, Milwaukee, Wis.). The reaction is stirred at room temperature for 24 hours and then 100 grams of terminal amine functional silicone (30,000 MW; DMS-A32 available from Gelest Co., Morrisville, Pa.) is added to the reaction. After 24 hours at 40° C., 1 gram of piperazine is added to the reactor and the reaction is continued for another 4 hours.

Example Polymer 9

2.69 grams of butanediol-diglycidyl ether and 0.57 grams of piperazine are charged to a reactor with 250 grams of tetrahydrofuran (available from Aldrich Chemical, Milwaukee, Wis.). The reaction is stirred at room temperature for 24 hours and then 100 grams of terminal amine functional silicone (30,000 MW; DMS-A32 available from Gelest Co., Morrisville, Pa.) is added to the reaction. After 24 hours at 40° C., 1 gram of piperazine is added to the reactor and the reaction is continued for another 4 hours.

Example 10

Quaternization of Example Polymer 1

50 grams of the copolymer from example 1 along with 200 ml of isopropyl alcohol (available from Aldrich Chemical, Milwaukee, Wis.) is added to a reactor along with 10 grams of ethyl bromide (available from Aldrich Chemical, Milwaukee, Wis.). This is stirred and heated at 40° C. for 24 hours. The quaternized polymer is isolated by vacuum stripping.

Example 11

Quaternization of Example Polymer 3

50 grams of the copolymer from example 3 along with 200 ml of isopropyl alcohol (available from Aldrich Chemical, Milwaukee, Wis.) is added to a reactor along with 10 grams of methyl chloride (available from Aldrich Chemical, Milwaukee, Wis.). This is stirred and heated at 100° C. for 24 hours under pressure. The quaternized polymer is isolated by vacuum stripping.

FORMULATION EXAMPLES

Hair Care Formulations

Any suitable method of making the shampoo of the present invention may be used. A typical procedure used would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step. Appropriate mixing steps to insure homogeneity are used as needed. The product is finished by the addition of pH control agents, hydrotropes, and salts to the desired physical properties

TABLE 1

Example Hair Care Shampoo Formulations

| EXAMPLE COMPOSITION | I | II | III | IV | V | VI |
| --- | --- | --- | --- | --- | --- | --- |
| Ingredient | | | | | | |
| Water | to 100% | to 100% | to 100% | to 100% | to 100% | to 100% |
| Polyquaternium 76 [1] | 0.25 | — | — | 0.25 | — | — |
| Guar, Hydroxypropyl Trimonium Chloride [2] | — | 0.25 | — | — | 0.25 | — |
| Polyquaternium 6 [3] | — | — | 0.79 | — | — | 0.79 |
| Sodium Laureth Sulfate (SLE3S) [4] | 21.43 | 21.43 | 21.43 | — | — | — |
| Sodium Laureth Sulfate (SLE1S) [4] | — | — | — | 10.50 | 10.50 | 10.50 |
| Sodium Lauryl Sulfate (SLS) [5] | 20.69 | 20.69 | 20.69 | 1.5 | 1.5 | 1.5 |
| Aminosiloxane Polymer [6,7] | 0.50 | 0.50 | 1.00 | 0.50 | 0.50 | 1.00 |
| Cocoamidopropyl Betaine [8] | 3.33 | 3.33 | 3.33 | 1.0 | 1.0 | 1.0 |
| Cocoamide MEA [9] | 1.0 | 1.0 | 1.0 | 1.0 | 1.0 | 1.0 |
| Ethylene Glycol Distearate [10] | 1.50 | 1.50 | 1.50 | 1.50 | 1.50 | 1.50 |
| Sodium Chloride [11] | 0.25 | 0.25 | 0.25 | 0.25 | 0.25 | 0.25 |
| Fragrance | 0.70 | 0.70 | 0.70 | 0.70 | 0.70 | 0.70 |
| Preservatives, pH adjusters | Up to 1% | Up to 1% | Up to 1% | Up to 1% | Up to 1% | Up to 1% |

[1] Mirapol ® AT-1, Copolymer of Acrylamide(AM) and TRIQUAT, MW = 1,000,000; CD = 1.6 meq./gram; 10% active; Supplier Rhodia
[2] Jaguar ® C500, MW—500,000, CD = 0.7, supplier Rhodia
[3] Mirapol ® 100S, 31.5% active, supplier Rhodia
[4] Sodium Laureth Sulfate, 28% active, supplier: P&G
[5] Sodium Lauryl Sulfate, 29% active supplier: P&G
[6] Aminosiloxane Polymer of Example 9 (mixtures thereof may also be used)
[7] Aminosiloxane Polymer of Example 11 (mixtures thereof may also be used)
[8] Tego ® betaine F-B, 30% active supplier: Goldschmidt Chemicals
[9] Monamid CMA, 85% active , supplier Goldschmidt Chemical
[10] Ethylene Glycol Distearate, EGDS Pure, supplier Goldschmidt Chemical
[11] Sodium Chloride USP (food grade), supplier Morton; note that salt is an adjustable ingredient, higher or lower levels may be added to achieve target viscosity.

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicone emulsion, or a blend of silicones and a low viscosity fluid, or an aqueous dispersion of a silicone is added to the gel matrix. The gel matrix is maintained at about 50° C. during this time with constant stirring to assure homogenization. After it is homogenized, it is cooled to room temperature. A triblender and/or mill can be used in each step, if necessary to disperse the materials.

TABLE 2

Example Hair Care Conditioner Formulations

| EXAMPLE COMPOSITION | I | II |
|---|---|---|
| Ingredient | | |
| Water | q.s. to 100% | q.s. to 100% |
| Aminosiloxane Polymer [1] | 1.0 | — |
| Aminosiloxane Polymer [2] | — | 1.0 |
| Cyclopentasiloxane [3] | — | 0.61 |
| Behenyl trimethyl ammonium chloride [4] | 2.25 | 2.25 |
| Isopropyl alcohol | 0.60 | 0.60 |
| Cetyl alcohol [5] | 1.86 | 1.86 |
| Stearyl alcohol [6] | 4.64 | 4.64 |
| Disodium EDTA | 0.13 | 0.13 |
| NaOH | 0.01 | 0.01 |
| Benzyl alcohol | 0.40 | 0.40 |
| Methylchloroisothiazolinone/Methylisothiazolinone [7] | 0.0005 | 0.0005 |
| Panthenol [8] | 0.10 | 0.10 |
| Panthenyl ethyl ether [9] | 0.05 | 0.05 |
| Fragrance | 0.35 | 0.35 |

[1] Amino Siloxane Polymer of Example 9 (mixtures thereof may also be used)
[2] Amino Siloxane Polymer of Example 11 (mixtures thereof may also be used)
[3] Cyclopentasiloxane: SF1202 available from Momentive Performance Chemicals
[4] Behenyl trimethyl ammonium chloride/Isopropyl alcohol: Genamin TM KMP available from Clariant
[5] Cetyl alcohol: Konol TM series available from Shin Nihon Rika
[6] Stearyl alcohol: Konol TM series available from Shin Nihon Rika
[7] Methylchloroisothiazolinone/Methylisothiazolinone: Kathon TM CG available from Rohm & Haas
[8] Panthenol: Available from Roche
[9] Panthenyl ethyl ether: Available from Roche Fabric Care Formulations Liquid detergent compositions are made by mixing together the ingredients listed below in the proportions shown:

TABLE 3

Example Fabric Care Formulations

| Ingredient (wt %) | I | II | III | IV | V |
|---|---|---|---|---|---|
| $C_{12}$—$C_{15}$ alkyl poly-ethoxylate (1.8) sulfate[1] | 20.1 | 16.6 | 14.7 | 13.9 | 8.2 |
| $C_{11.8}$ linear alkylbenzene sulfonic acid[2] | — | 4.9 | 4.3 | 4.1 | 8.2 |
| $C_{16}$—$C_{17}$ branched alkyl sulfate[1] | — | 2.0 | 1.8 | 1.6 | — |
| $C_{12}$ alkyl trimethyl ammonium chloride[4] | 2.0 | — | — | — | — |
| $C_{12}$ alkyl dimethyl amine oxide[5] | — | 0.7 | 0.6 | — | — |
| $C_{12}$—$C_{14}$ alcohol 9 ethoxylate[3] | 0.3 | 0.8 | 0.9 | 0.6 | 0.7 |
| $C_{15}$—$C_{16}$ branched alcohol-7 ethoxylate[1] | — | — | — | — | 4.6 |
| 1,2 Propane diol[6] | 4.5 | 4.0 | 3.9 | 3.1 | 2.3 |
| Ethanol | 3.4 | 2.3 | 2.0 | 1.9 | 1.2 |
| $C_{12}$—$C_{18}$ Fatty Acid[5] | 2.1 | 1.7 | 1.5 | 1.4 | 3.2 |
| Citric acid | 3.4 | 3.2 | 3.5 | 2.7 | 3.9 |
| Protease[7] (32 g/L) | 0.42 | 1.3 | 0.07 | 0.5 | 1.12 |
| Fluorescent Whitening Agent[8] | 0.08 | 0.2 | 0.2 | 0.17 | 0.18 |
| Diethylenetriamine pentaacetic acid[6] | 0.5 | 0.3 | 0.3 | 0.3 | 0.2 |
| Ethoxylated polyamine[9] | 0.7 | 1.8 | 1.5 | 2.0 | 1.9 |
| Grease Cleaning Alkoxylated Polyalkylenimine Polymer[10] | — | — | 1.3 | 1.8 | — |
| Zwitterionic ethoxylated quaternized sulfated hexamethylene diamine[11] | — | 1.5 | — | — | 0.8 |
| Hydrogenated castor oil[12] | 0.2 | 0.2 | — | 0.12 | 0.3 |
| Copolymer of acrylamide and methacrylamidopropyl trimethyl-ammonium chloride[13] | 0.3 | 0.2 | 0.3 | 0.1 | 0.3 |
| Aminosiloxane Polymer[16, 17, 18] | 6.0 | 6.0 | 3.0 | 0.5 | 3.0 |
| Water, perfumes, dyes, buffers, solvents and other optional components | to 100% pH 8.0-8.2 | to 100% pH 8.0-8.2 | to 100% pH 8.0-8.2 | to 100% pH 8.0-8.2 | to 100% pH 8.0-8.2 |

| Ingredient (wt %) | VI | VII | VIII | IX | X |
|---|---|---|---|---|---|
| $C_{12}$—$C_{15}$ alkyl poly-ethoxylate (3.0) sulfate[1] | 8.5 | 2.9 | 2.9 | 2.9 | 6.8 |
| $C_{11.8}$ linear alkylbenzene sulfonic acid[2] | 11.4 | 8.2 | 8.2 | 8.2 | 1.2 |
| $C_{14}$—$C_{15}$ alkyl 7-ethoxylate[1] | — | 5.4 | 5.4 | 5.4 | 3.0 |
| $C_{12}$—$C_{14}$ alkyl 7-ethoxylate[3] | 7.6 | — | — | — | 1.0 |
| 1,2 Propane diol | 6.0 | 1.3 | 1.3 | 6.0 | 0.2 |
| Ethanol | — | 1.3 | 1.3 | — | 1.4 |
| Di Ethylene Glycol | 4.0 | — | — | — | — |
| Na Cumene Sulfonate | — | 1.0 | 1.0 | 0.9 | — |
| $C_{12}$—$C_{18}$ Fatty Acid[5] | 9.5 | 3.5 | 3.5 | 3.5 | 4.5 |
| Citric acid | 2.8 | 3.4 | 3.4 | 3.4 | 2.4 |
| Protease (40.6 mg/g)[7] | 1.0 | 0.6 | 0.6 | 0.6 | 0.3 |
| Natalase 200 L (29.26 mg/g)[14] | — | 0.1 | 0.1 | 0.1 | — |
| Termamyl Ultra (25.1 mg/g)[14] | 0.7 | 0.1 | 0.1 | 0.1 | 0.1 |
| Mannaway 25 L (25 mg/g)[14] | 0.1 | 0.1 | 0.1 | 0.1 | 0.02 |
| Whitezyme ® (20 mg/g)[14] | 0.2 | 0.1 | 0.1 | 0.1 | — |
| Fluorescent Whitening Agent[8] | 0.2 | 0.1 | 0.1 | 0.1 | — |
| Diethylene Triamine Penta Methylene Phosphonic acid | — | 0.3 | 0.3 | 0.3 | 0.1 |
| Hydroxy Ethylidene 1,1 Di Phosphonic acid | 1.5 | — | — | — | — |
| Zwitterionic ethoxylated quaternized sulfated hexamethylene diamine[11] | 2.1 | 1.0 | 1.0 | 1.0 | 0.7 |
| Grease Cleaning Alkoxylated Polyalkylenimine Polymer[10] | — | 0.4 | 0.4 | 0.4 | — |
| PEG-PVAc Polymer[15] | 0.9 | 0.5 | 0.5 | 0.5 | — |
| Hydrogenated castor oil[12] | 0.8 | 0.4 | 0.4 | 0.4 | 0.3 |
| Terpolymer of acrylamide, acrylic acid and methacrylamidopropyl trimethylammonium chloride[13] | — | 0.2 | 0.2 | 0.2 | 0.2 |

TABLE 3-continued

Example Fabric Care Formulations

| | | | | | |
|---|---|---|---|---|---|
| Borate | — | 1.3 | — | — | 1.2 |
| 4 Formyl Phenyl Boronic Acid | — | — | 0.025 | — | — |
| Aminosiloxane Polymer[16,17,18] | 3.0 | 4.5 | 2.0 | 3.0 | 4.5 |
| Water, perfumes, dyes, buffers, neutralizers, stabilizers and other optional components | to 100% pH 8.0-8.2 | to 100% pH 8.0-8.2 | to 100% pH 8.0-8.2 | to 100% pH 8.0-8.2 | to 100% pH 8.0-8.2 |

[1]Available from Shell Chemicals, Houston, TX.
[2]Available from Huntsman Chemicals, Salt Lake City, UT.
[3]Available from Sasol Chemicals, Johannesburg, South Africa
[4]Available from Evonik Corporation, Hopewell, VA.
[5]Available from The Procter & Gamble Company, Cincinnati, OH.
[6]Available from Sigma Aldrich chemicals, Milwaukee, WI
[7]Available from Genencor International, South San Francisco, CA.
[8]Available from Ciba Specialty Chemicals, High Point, NC
[9]600 g/mol molecular weight polyethylenimine core with 20 ethoxylate groups per —NH and available from BASF (Ludwigshafen, Germany)
[10]600 g/mol molecular weight polyethylenimine core with 24 ethoxylate groups per —NH and 16 propoxylate groups per —NH. Available from BASF (Ludwigshafen, Germany).
[11]Described in WO 01/05874 and available from BASF (Ludwigshafen, Germany)
[12]Available under the tradename ThixinR from Elementis Specialties, Highstown, NJ
[13]Available from Nalco Chemicals, Naperville, IL.
[14]Available from Novozymes, Copenhagen, Denmark.
[15]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).
[16]Amino Siloxane Polymer of Example 2 (mixtures thereof may also be used)
[17]Amino Siloxane Polymer of Example 8 (mixtures thereof may also be used)
[18]Amino Siloxane Polymer of Example 10 (mixtures thereof may also be used)

TABLE 4

Example Rinse-added Fabric Care Formulations
Rinse-Added fabric care compositions are prepared by mixing together ingredients shown below:

| Ingredient | I | II | III | IV |
|---|---|---|---|---|
| Fabric Softener Active[1] | 16.2 | 11.0 | 16.2 | — |
| Fabric Softener Active[2] | — | — | — | 5.0 |
| Cationic Starch[3] | 1.5 | — | 1.5 | — |
| Polyethylene imine[4] | 0.25 | 0.25 | — | — |
| Quaternized polyacrylamide[5] | — | — | 0.25 | 0.25 |
| Calcium chloride | 0.15 | 0. | 0.15 | — |
| Ammonium chloride | 0.1 | 0.1 | 0.1 | — |
| Suds Suppressor[6] | — | — | — | 0.1 |
| Aminosiloxane Polymer[7,8,9] | 2.0 | 5.0 | 2.0 | 2.0 |
| Perfume | 0.85 | 2.0 | 0.85 | 1.0 |
| Perfume microcapsule[10] | 0.65 | 0.75 | 0.65 | 0.3 |
| Water, suds suppressor, stabilizers, pH control agents, buffers, dyes & other optional ingredients | to 100% pH = 3.0 | to 100% pH = 3.0 | to 100% pH = 3.0 | to 100% pH = 3.0 |

[1]N,N di(tallowoyloxyethyl)-N,N dimethylammonium chloride available from Evonik Corporation, Hopewell, VA.
[2]Reaction product of fatty acid with Methyldiethanolamine, quaternized with Methylchloride, resulting in a 2.5:1 molar mixture of N,N-di(tallowoyloxyethyl) N,N-dimethylammonium chloride and N-(tallowoyloxyethyl) N-hydroxyethyl N,N-dimethylammonium chloride available from Evonik Corporation, Hopewell, VA.
[3]Cationic starch based on common maize starch or potato starch, containing 25% to 95% amylase and a degree of substitution of from 0.02 to 0.09, and having a viscosity measured as Water Fluidity having a value from 50 to 84. Available from National Starch, Bridgewater, NJ
[4]Available from Nippon Shokubai Company, Tokyo, Japan under the trade name Epomin ® 1050.
[5]Cationic polyacrylamide polymer such as a copolymer of acrylamide/[2-(acryloylamino) ethyl]tri-methylammonium chloride (quaternized dimethyl aminoethyl acrylate) available from BASF, AG, Ludwigshafen under the trade name Sedipur ® 544.
[6]SILFOAM ® SE90 available from Wacker AG of Munich, Germany
[7]Amino Siloxane Polymer of Example 2 (mixtures thereof may also be used)
[8]Amino Siloxane Polymer of Example 8 (mixtures thereof may also be used)
[9]Amino Siloxane Polymer of Example 10 (mixtures thereof may also be used)
[10]Available from Appleton Paper of Appleton, WI Personal Care Formulation Lotions for Personal and Feminine care compositions are prepared by mixing the following ingredients:

TABLE 5

Example Personal Care Formulations

| Ingredient | I | II |
|---|---|---|
| Polyethylene glycol-200[1] | 40.3 | — |
| Glycerin[2] | 40.3 | — |
| Amino Siloxane Polymer[3,4] | 3.7 | 3.7 |
| Water | to 100% | to 100% |

[1]Available from Sigma Aldrich chemicals, Milwaukee, WI
[2]Available from Sigma Aldrich chemicals, Milwaukee, WI
[3]Amino Siloxane Polymer of Example 2 (mixtures thereof may also be used)
[4]Amino Siloxane Polymer of Example 11 (mixtures thereof may also be used)

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A polysiloxane copolymer having the following structure:

$$D_z\text{-}(E\text{-}B)_x\text{-}A\text{-}(B\text{-}E)_x\text{-}D_z$$

wherein:
each index x is independently an integer from 1 to 20, and
each z is independently 0 or 1;
A has the following structure:

$$\text{—N(H)—R}_2\text{—}\left[\text{Si}(R_1)(R_1)\text{—O}\right]_n\text{—Si}(R_1)(R_1)\text{—R}_2\text{—N(H)—}$$

wherein:
each $R_1$ is independently a H, —OH, or $C_1$-$C_{22}$ alkyl group;
each $R_2$ is independently selected from a divalent $C_1$-$C_{22}$ alkylene radical, a divalent $C_2$-$C_{12}$ alkylene radical, a divalent linear $C_2$-$C_8$ alkylene radical, or a divalent linear $C_3$-$C_4$ alkylene radical;
the index n is an integer from 1 to about 5,000;
each B is independently selected from the following moieties:

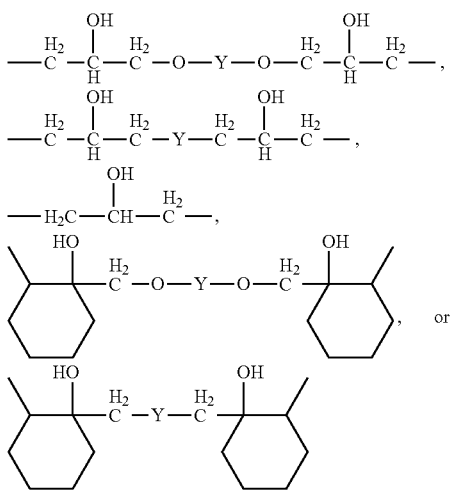

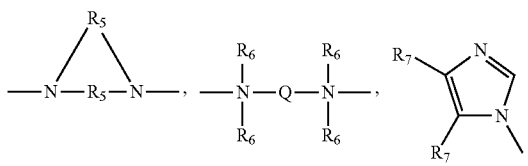

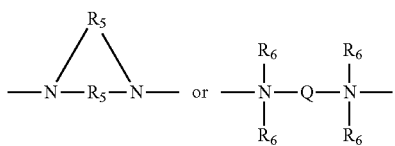

wherein for each structure, Y is a divalent $C_2$-$C_{22}$ alkylene radical that is optionally interrupted by one or more heteroatoms selected from the group consisting of O, P, S, N and combinations thereof or a divalent $C_8$-$C_{22}$ aryl alkylene radical;

each E is independently selected from the following moieties:

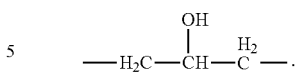

wherein:
each $R_5$ and each Q is independently selected from a divalent $C_1$-$C_{12}$ linear or branched aliphatic hydrocarbon radical that is optionally interrupted by one or more heteroatoms selected from the group consisting of O, P, S, N and combinations thereof;
each $R_6$ and $R_7$ is independently selected from H, $C_1$-$C_{20}$ alkyl, $C_1$-$C_{20}$ substituted alkyl, $C_6$-$C_{20}$ aryl, and $C_6$-$C_{20}$ substituted aryl, with the proviso that at least one $R_6$ on each of the nitrogen atoms is H; and when E is selected from

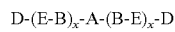

and when z is 1, the respective D is selected from H, —$CH_3$; or $R_6$; when E is

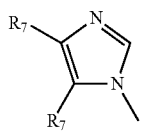

z is 0 and B is

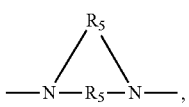

2. A composition comprising a polysiloxane copolymer according to claim 1 and comprising at least one additional component selected from the group consisting of emollients, emulsifiers and surfactants, thickeners/viscosity regulators/stabilizers, UV light protection filters, antioxidants, hydrotropes or polyols, solids and fillers, film formers, pearlescent additives, insect repellents, preservatives, conditioners, perfumes, dyes, care additives, solvents, perfume delivery systems, fluorescent whitening agents, enzymes, rheology modifiers, builders, bleaching agents, bleach activators, bleach boosters, chelants, stabilizers, softening actives, high melting point fatty compounds, polymers, anti-dandruff actives, humectant, suspending agents, skin care actives, color cosmetics, and mixtures thereof.

3. The composition of claim 2, said composition comprising, based on total composition weight, from about 0.01% to about 70% of said polysiloxane copolymer.

4. The composition of claim 2 wherein said polysiloxane copolymer having the following structure:

$D\text{-}(E\text{-}B)_x\text{-}A\text{-}(B\text{-}E)_x\text{-}D$ wherein:
each index x is independently an integer from 2 to 6;
A has the following structure:

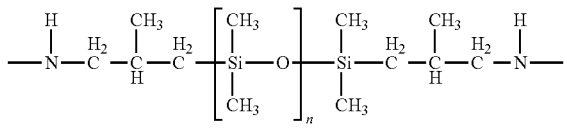

wherein:
the index n is from about 250 to about 700;
each B is independently selected from a moiety having the following structure:

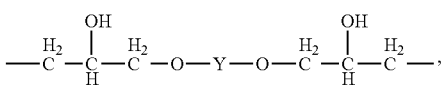

wherein Y is a divalent $C_2$-$C_6$ alkylene radical;
each E is

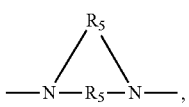

wherein each $R_5$ is —$CH_2CH_2$—:
each D is H.

5. A composition according to claim 1 wherein said polysiloxane copolymer comprises a quaternizing moiety selected from the group consisting of $C_1$-$C_{30}$ alkyl halide, $C_1$-$C_{30}$ aryl halide, $C_1$-$C_{30}$ alkyl sulfate, and/or $C_1$-$C_{30}$ aryl sulfates.

6. A composition according to claim 2 wherein said composition comprises from about 0.1% to about 50% by weight of a surfactant selected from the group consisting of anionic, cationic, amphoteric, nonionic surfactants, and combinations thereof.

7. A composition according to claim 6 comprising a material selected from the group consisting of fluorescent whitening agents, enzymes, rheology modifiers, builders, bleaching agents, bleach activators, bleach boosters, chelants, and mixtures thereof, wherein the weight ratio of anionic surfactant to the sum of cationic, amphoteric, and nonionic surfactants is from about 10:1 to about 1:10 and the total weight percent of surfactant is said composition is from about 5% to about 50%, or from about 7% to about 30%.

8. A composition according the claim 2 comprising one or more adjuncts selected from the group consisting of:
  a) an anionic surfactant selected from the group consisting of a $C_{11}$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, alkyls, alkyl ether sulfates, succinnates, olefin sulfonates, beta-alkyloxy alkane sulfonates and mixtures thereof,
  b) a cationic surfactant selected from the group consisting of mono-long alkyl quaternized ammonium salt cationic surfactants, mono-alkyl amines, di-alkyl chain cationic surfactants, and mixtures thereof,
  c) a conditioning active selected from the group consisting of silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein,
  d) a perfume delivery system selected from a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, a pro-perfume, low odor detection threshold perfume ingredients, wherein said low odor detection threshold perfume ingredients may comprise less than about 25%, by weight of the total neat perfume composition, and mixtures thereof,
  e) a perfume comprising a perfume raw material selected from the group consisting of perfumes such as 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, α-damascone, β-damascone, δ-damascone, β-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and β-dihydro ionone, linalool, ethyllinalool, tetrahydrolinalool, and dihydromyrcenol,
  f) a softening active selected from the group consisting of from the group consisting of polyglycerol esters, oily sugar derivatives, wax emulsions, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate and mixtures thereof,
  g) a deposition aid polymer selected from the group consisting of starch, guar, cellulose, cassia, locust bean, Konjac, Tara, galactomannan, polyDADMAC, Tapioca starch, polyTriquat, and mixtures thereof,
  h) a deposition aid polymer selected from the group consisting of a cationic polymer having a cationic charge from about 0.005 meq/g to about 23 meq/g at the pH of said composition,
  i) a high melting point fatty compound selected from the group consisting of fatty alcohols, fatty acids, fatty alcohol derivatives, fatty acid derivatives, and mixtures thereof.

9. A method of treating and/or cleaning a situs, said method comprising
  a) optionally washing, rinsing and/or drying said situs;
  b) contacting said situs with a composition according to any one of claims 1-8; and
  c) optionally washing, rinsing and/or drying said situs.

* * * * *